United States Patent
Brucker et al.

(10) Patent No.: US 8,632,579 B2
(45) Date of Patent: *Jan. 21, 2014

(54) BIFURCATED STENT AND DELIVERY SYSTEM

(75) Inventors: Gregory G. Brucker, Minneapolis, MN (US); Enrique Malaret, Plymouth, MN (US); Todd Hall, Goshen, KY (US); David Byrd, Louisville, KY (US); Gerald Hubbs, Louisville, KY (US); Gregory Furnish, Louisville, KY (US); Josh Barber, Louisville, KY (US); Indaka Gunasekara, Louisville, KY (US); Benjamin Morris, Louisville, KY (US); Valerie Futral Maron, Louisville, KY (US); Sava A. Chernomordik, Louisville, KY (US); William C. Mers Kelly, Crestwood, KY (US); William A. Reuss, Jr., Louisville, KY (US); Simon Furnish, New York City, NY (US); Michael W. Wilson, LaGrange, KY (US); Hacene Bouadi, Palo Alto, CA (US); John C. Muskivitch, Cupertino, CA (US); Matthew L. Pease, Mountain View, CA (US); David A. Rahdert, San Francisco, CA (US); Travis Rowe, Fremont, CA (US); Gregory M. Ruhf, Cupertino, CA (US); Brandon G. Walsh, Livermore, CA (US); Claude A. Vidal, Santa Barbara, CA (US); Thomas Banks, Santa Barbara, CA (US); Russ J. Redmond, Goleta, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 304 days.

This patent is subject to a terminal disclaimer.

(21) Appl. No.: 12/882,726

(22) Filed: Sep. 15, 2010
(Under 37 CFR 1.47)

(65) Prior Publication Data
US 2011/0004287 A1    Jan. 6, 2011

Related U.S. Application Data

(63) Continuation of application No. 10/083,707, filed on Feb. 26, 2002, now Pat. No. 7,799,064.

(60) Provisional application No. 60/271,506, filed on Feb. 26, 2001, provisional application No. 60/271,602, filed on Feb. 26, 2001, provisional application No. 60/271,595, filed on Feb. 26, 2001.

(51) Int. Cl.
*A61F 2/06* (2013.01)

(52) U.S. Cl.
USPC ............................................... 623/1.11

(58) Field of Classification Search
USPC .................. 623/1.11, 1.23, 2.11; 606/108, 606/191–200; 604/96.01, 509, 907–921
See application file for complete search history.

(56) References Cited

U.S. PATENT DOCUMENTS

| 1,861,769 A | 6/1932 | Wappler |
| 2,845,959 A | 8/1958 | Sidebotham |

(Continued)

FOREIGN PATENT DOCUMENTS

| CA | 2220864 | 7/1999 |
| DE | 29701758 | 5/1997 |

(Continued)

*Primary Examiner* — Melanie Tyson
(74) *Attorney, Agent, or Firm* — Seager, Tufte & Wickhem LLC

(57) ABSTRACT

Systems for delivering a bifurcated stent to a bifurcation site include catheters and/or bifurcated systems delivered therefrom. A catheter includes a balloon with a bulge region that allows a portion of the stent to be expanded.

20 Claims, 15 Drawing Sheets

(56) References Cited

U.S. PATENT DOCUMENTS

| | | | |
|---|---|---|---|
| 4,413,989 A | 11/1983 | Schjeldahl et al. | |
| 4,454,887 A | 6/1984 | Kruger | |
| 4,730,616 A | 3/1988 | Frisbie et al. | |
| 4,769,005 A | 9/1988 | Ginsburg et al. | |
| 4,774,949 A | 10/1988 | Fogarty | |
| 4,896,670 A | 1/1990 | Crittenden | |
| 4,905,667 A | 3/1990 | Foerster et al. | |
| 4,957,508 A | 9/1990 | Kaneko et al. | |
| 4,983,166 A | 1/1991 | Yamawaki | |
| 4,994,071 A | 2/1991 | MacGregor | |
| 5,156,620 A | 10/1992 | Pigott | |
| 5,219,355 A | 6/1993 | Parodi et al. | |
| 5,320,605 A | 6/1994 | Sahota | |
| 5,342,387 A | 8/1994 | Summers | |
| 5,443,497 A | 8/1995 | Venbrux | |
| 5,575,771 A | 11/1996 | Walinsky | |
| 5,599,300 A | 2/1997 | Weaver et al. | |
| 5,607,444 A | 3/1997 | Lam | |
| 5,613,980 A | 3/1997 | Chauhan | |
| 5,617,878 A | 4/1997 | Taheri | |
| 5,632,762 A | 5/1997 | Myler | |
| 5,632,763 A | 5/1997 | Glastra | |
| 5,639,278 A | 6/1997 | Dereume et al. | |
| 5,669,924 A | 9/1997 | Shaknovich | |
| 5,672,153 A | 9/1997 | Lax et al. | |
| 5,683,450 A | 11/1997 | Goicoechea et al. | |
| 5,693,086 A | 12/1997 | Goicoechea et al. | |
| 5,697,971 A | 12/1997 | Fischell et al. | |
| 5,720,735 A | 2/1998 | Dorros | |
| 5,749,825 A | 5/1998 | Fischell et al. | |
| 5,749,890 A | 5/1998 | Shaknovich | |
| 5,755,734 A | 5/1998 | Richter et al. | |
| 5,755,735 A | 5/1998 | Richter et al. | |
| 5,755,770 A | 5/1998 | Ravenscroft | |
| 5,755,771 A | 5/1998 | Penn et al. | |
| 5,755,772 A | 5/1998 | Evans et al. | |
| 5,755,773 A | 5/1998 | Evans et al. | |
| 5,755,778 A | 5/1998 | Kleshinski | |
| 5,776,101 A | 7/1998 | Goy | |
| 5,782,906 A | 7/1998 | Marshall et al. | |
| 5,800,508 A | 9/1998 | Goicoechea et al. | |
| 5,800,520 A | 9/1998 | Fogarty et al. | |
| 5,827,320 A | 10/1998 | Richter et al. | |
| 5,843,116 A * | 12/1998 | Crocker et al. | 606/192 |
| 5,855,600 A | 1/1999 | Alt | |
| 5,868,777 A | 2/1999 | Lam | |
| 5,893,887 A | 4/1999 | Jayaraman | |
| 5,906,640 A | 5/1999 | Penn et al. | |
| 5,916,263 A | 6/1999 | Goicoechea et al. | |
| 5,921,995 A | 7/1999 | Kleshinski | |
| 5,935,135 A | 8/1999 | Bramfitt et al. | |
| 5,938,696 A | 8/1999 | Goicoechea et al. | |
| 5,961,490 A | 10/1999 | Adams | |
| 5,961,548 A | 10/1999 | Shmulewitz | |
| 5,968,089 A | 10/1999 | Krajicek | |
| 5,972,017 A | 10/1999 | Berg et al. | |
| 5,984,955 A | 11/1999 | Wisselink | |
| 5,993,481 A | 11/1999 | Marcade et al. | |
| 6,013,054 A | 1/2000 | Jiun Yan | |
| 6,016,810 A | 1/2000 | Ravenscroft | |
| 6,017,324 A | 1/2000 | Tu et al. | |
| 6,017,363 A | 1/2000 | Jojeibane | |
| 6,030,414 A | 2/2000 | Taheri | |
| 6,033,434 A | 3/2000 | Borghi | |
| 6,033,435 A | 3/2000 | Penn et al. | |
| 6,039,758 A | 3/2000 | Quiachon et al. | |
| 6,045,557 A | 4/2000 | White et al. | |
| 6,048,360 A | 4/2000 | Khosravi et al. | |
| 6,048,361 A | 4/2000 | Von Oepen | |
| 6,051,020 A | 4/2000 | Goicoechea et al. | |
| 6,056,722 A | 5/2000 | Jayaraman | |
| 6,056,775 A | 5/2000 | Borghi et al. | |
| 6,059,824 A | 5/2000 | Taheri | |
| 6,068,655 A | 5/2000 | Seguin et al. | |
| 6,086,611 A | 7/2000 | Duffy et al. | |
| 6,090,133 A | 7/2000 | Richter et al. | |
| 6,093,203 A | 7/2000 | Uflacker | |
| 6,096,073 A | 8/2000 | Webster et al. | |
| 6,099,558 A | 8/2000 | White | |
| 6,099,560 A | 8/2000 | Penn et al. | |
| 6,102,938 A | 8/2000 | Evans et al. | |
| 6,117,117 A | 9/2000 | Mauch | |
| 6,117,156 A | 9/2000 | Richter et al. | |
| 6,129,738 A | 10/2000 | Lashinski et al. | |
| 6,129,754 A | 10/2000 | Kanesaka et al. | |
| 6,132,459 A | 10/2000 | Piplani et al. | |
| 6,142,973 A | 11/2000 | Carleton et al. | |
| 6,143,002 A | 11/2000 | Vietmeier | |
| 6,159,238 A | 12/2000 | Killion et al. | |
| 6,165,195 A | 12/2000 | Wilson et al. | |
| 6,165,213 A | 12/2000 | Goicoechea et al. | |
| 6,168,621 B1 | 1/2001 | Vrba | |
| 6,183,509 B1 | 2/2001 | Dibie | |
| 6,197,046 B1 | 3/2001 | Piplani et al. | |
| 6,197,049 B1 | 3/2001 | Shaolian et al. | |
| 6,210,380 B1 | 4/2001 | Mauch | |
| 6,210,429 B1 | 4/2001 | Vardi et al. | |
| 6,210,431 B1 | 4/2001 | Power | |
| 6,210,433 B1 | 4/2001 | Larre | |
| 6,217,527 B1 | 4/2001 | Selmon et al. | |
| 6,221,080 B1 | 4/2001 | Power | |
| 6,221,090 B1 | 4/2001 | Wilson | |
| 6,221,098 B1 | 4/2001 | Wilson et al. | |
| 6,231,563 B1 | 5/2001 | White et al. | |
| 6,231,598 B1 | 5/2001 | Berry et al. | |
| 6,238,430 B1 | 5/2001 | Klumb et al. | |
| 6,248,122 B1 | 6/2001 | Klumb et al. | |
| 6,251,133 B1 | 6/2001 | Richter et al. | |
| 6,254,593 B1 | 7/2001 | Wilson | |
| 6,258,073 B1 | 7/2001 | Mauch | |
| 6,258,099 B1 * | 7/2001 | Mareiro et al. | 606/108 |
| 6,258,115 B1 | 7/2001 | Dubrul | |
| 6,258,116 B1 | 7/2001 | Hojeibane | |
| 6,261,273 B1 | 7/2001 | Ruiz | |
| 6,261,305 B1 * | 7/2001 | Marotta et al. | 606/200 |
| 6,261,316 B1 | 7/2001 | Shaolian et al. | |
| 6,264,662 B1 | 7/2001 | Lauterjung | |
| 6,264,686 B1 | 7/2001 | Rieu et al. | |
| 6,273,909 B1 | 8/2001 | Kugler et al. | |
| 6,287,277 B1 | 9/2001 | Yan | |
| 6,290,673 B1 | 9/2001 | Shanley | |
| 6,302,906 B1 | 10/2001 | Goicoechea et al. | |
| 6,302,908 B1 | 10/2001 | Parodi | |
| 6,306,164 B1 | 10/2001 | Kujawski | |
| 6,312,461 B1 | 11/2001 | Unsworth et al. | |
| 6,319,278 B1 | 11/2001 | Quinn et al. | |
| 6,322,587 B1 | 11/2001 | Quiachon et al. | |
| 6,325,819 B1 | 12/2001 | Pavcnik et al. | |
| 6,325,822 B1 | 12/2001 | Chouinard et al. | |
| 6,325,826 B1 | 12/2001 | Vardi et al. | |
| 6,334,864 B1 | 1/2002 | Amplatz et al. | |
| 6,383,213 B2 | 5/2002 | Wilson et al. | |
| 6,387,120 B2 | 5/2002 | Wilson et al. | |
| 6,494,905 B1 | 12/2002 | Zedler et al. | |
| 7,799,064 B2 * | 9/2010 | Brucker et al. | 623/1.11 |
| 2001/0002443 A1 | 5/2001 | Parodi | |
| 2001/0002927 A1 | 6/2001 | Detampel | |
| 2001/0002943 A1 | 6/2001 | Nagayama et al. | |
| 2001/0003161 A1 | 6/2001 | Vardi et al. | |
| 2001/0004705 A1 | 6/2001 | Killion et al. | |
| 2001/0004706 A1 | 6/2001 | Hojeibane | |
| 2001/0004707 A1 | 6/2001 | Dereume et al. | |
| 2001/0004823 A1 | 6/2001 | Cronin et al. | |
| 2001/0007954 A1 | 7/2001 | Shaolian et al. | |
| 2001/0016766 A1 | 8/2001 | Vardi et al. | |
| 2001/0016767 A1 | 8/2001 | Wilson et al. | |
| 2001/0016768 A1 | 8/2001 | Wilson et al. | |
| 2001/0020173 A1 | 9/2001 | Klumb et al. | |
| 2001/0020184 A1 | 9/2001 | Dehdashtian et al. | |
| 2001/0025195 A1 | 9/2001 | Shaolian et al. | |

(56) References Cited

U.S. PATENT DOCUMENTS

2001/0027291 A1    10/2001    Shanley
2001/0029396 A1    10/2001    Wilson et al.

FOREIGN PATENT DOCUMENTS

| | | |
|---|---|---|
| DE | 29701883 | 5/1997 |
| EP | 0347023 | 12/1989 |
| EP | 0479557 | 4/1992 |
| EP | 0479730 | 4/1992 |
| EP | 0686379 | 12/1995 |
| EP | 0751752 | 1/1997 |
| EP | 0783873 | 7/1997 |
| EP | 0804907 | 11/1997 |
| EP | 0808140 | 11/1997 |
| EP | 0862392 | 9/1998 |
| EP | 0880949 | 12/1998 |
| EP | 0883384 | 12/1998 |
| EP | 0897700 | 2/1999 |
| EP | 0904745 | 3/1999 |
| EP | 0937442 | 8/1999 |
| EP | 1031329 | 8/2000 |
| EP | 1031330 | 8/2000 |
| FR | 2678508 | 1/1993 |
| FR | 2740346 | 4/1997 |
| FR | 2756173 | 5/1998 |
| FR | 2760351 | 9/1998 |
| GB | 2337002 | 11/1999 |
| WO | WO 94/00179 | 1/1994 |
| WO | WO 95/10442 | 4/1995 |
| WO | WO 95/21592 | 8/1995 |
| WO | WO 96/34580 | 11/1996 |
| WO | WO 96/41592 | 12/1996 |
| WO | WO 97/07752 | 3/1997 |
| WO | WO 97/15346 | 5/1997 |
| WO | WO 97/16217 | 5/1997 |
| WO | WO 97/41803 | 11/1997 |
| WO | WO 97/46174 | 12/1997 |
| WO | WO 98/19628 | 5/1998 |
| WO | WO 98/36709 | 8/1998 |
| WO | WO 98/37833 | 9/1998 |
| WO | WO 98/47446 | 10/1998 |
| WO | WO 98/47447 | 10/1998 |
| WO | WO 98/48879 | 11/1998 |
| WO | WO 98/53759 | 12/1998 |
| WO | WO 99/03426 | 1/1999 |
| WO | WO 99/03462 | 1/1999 |
| WO | WO 99/04726 | 2/1999 |
| WO | WO 99/13808 | 3/1999 |
| WO | WO 99/15108 | 4/1999 |
| WO | WO 99/15109 | 4/1999 |
| WO | WO 99/24104 | 5/1999 |
| WO | WO 99/34749 | 7/1999 |
| WO | WO 99/36002 | 7/1999 |
| WO | WO 99/36015 | 7/1999 |
| WO | WO 99/44539 | 9/1999 |
| WO | WO 99/56661 | 11/1999 |
| WO | WO 99/65419 | 12/1999 |
| WO | WO 00/07523 | 2/2000 |
| WO | WO 00/10485 | 3/2000 |
| WO | WO 00/10489 | 3/2000 |
| WO | WO 00/13613 | 3/2000 |
| WO | WO 00/16719 | 3/2000 |
| WO | WO 00/27307 | 5/2000 |
| WO | WO 00/27463 | 5/2000 |
| WO | WO 00/28922 | 5/2000 |
| WO | WO 00/32266 | 6/2000 |
| WO | WO 00/44307 | 8/2000 |
| WO | WO 00/44309 | 8/2000 |
| WO | WO 00/47134 | 8/2000 |
| WO | WO 00/48531 | 8/2000 |
| WO | WO 00/49951 | 8/2000 |
| WO | WO 00/51523 | 9/2000 |
| WO | WO 00/57813 | 10/2000 |
| WO | WO 00/67673 | 11/2000 |
| WO | WO 00/71055 | 11/2000 |
| WO | WO 00/74595 | 12/2000 |
| WO | WO 01/021095 | 3/2001 |
| WO | WO 01/21109 | 3/2001 |
| WO | WO 01/21244 | 3/2001 |
| WO | WO 01/30433 | 5/2001 |
| WO | WO 01/35715 | 5/2001 |
| WO | WO 01/35863 | 5/2001 |
| WO | WO 01/39697 | 6/2001 |
| WO | WO 01/39699 | 6/2001 |
| WO | WO 01/41677 | 6/2001 |
| WO | WO 01/43665 | 6/2001 |
| WO | WO 01/43809 | 6/2001 |
| WO | WO 01/45594 | 6/2001 |
| WO | WO 01/45785 | 6/2001 |
| WO | WO 01/49342 | 7/2001 |
| WO | WO 01/54621 | 8/2001 |
| WO | WO 01/54622 | 8/2001 |
| WO | WO 01/58385 | 8/2001 |
| WO | WO 01/60284 | 8/2001 |
| WO | WO 01/70294 | 9/2001 |
| WO | WO 01/70299 | 9/2001 |
| WO | WO 01/74273 | 10/2001 |
| WO | WO 01/89409 | 11/2001 |
| WO | WO 02/39888 | 5/2002 |
| WO | WO 02/39926 | 5/2002 |

\* cited by examiner

BIFURCATED STENT AND DELIVERY SYSTEM

CROSS-REFERENCE TO RELATED APPLICATIONS

This application is a continuation of U.S. application Ser. No. 10/083,707, filed Feb. 26, 2002, now issued as U.S. Pat. No. 7,799,064, which claims priority to U.S. provisional application 60/271,506 filed Feb. 26, 2001; U.S. provisional application 60/271,602 filed Feb. 26, 2001; and U.S. provisional application 60/271,595 filed Feb. 26, 2001; the entire content of each being incorporated herein by reference.

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding or expanded by an internal radial force, such as when mounted on a balloon.

Stents are generally tubular devices for insertion into body lumens. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Stents may be constructed from a variety of materials such as stainless steel, Elgiloy®, nitinol, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired tubular or bifurcated tubular shape of the stent; one or more wires or ribbons of stent material may be braided or otherwise formed into a desired shape and pattern.

A vessel having a stenosis may be viewed as an inwardly protruding arcuate addition of hardened material to a cylindrical vessel wall, where the stenosed region presents a somewhat rigid body attached along, and to, the elastic wall. The stenosis presents resistance to any expansion of the vessel in the region bridged by the stenosis. Stenoses vary in composition, for example, in the degree of calcification, and therefore vary in properties as well.

A stent may be used to provide a prosthetic intraluminal wall, e.g., in the case of a stenosis to provide an unobstructed conduit for blood in the area of the stenosis. An endoluminal prosthesis comprises a stent which carries a prosthetic graft layer of fabric and is used, e.g., to treat an aneurysm by removing the pressure on a weakened part of an artery so as to reduce the risk of embolism, or of the natural artery wall bursting. Typically, a stent or endoluminal prosthesis is implanted in a blood vessel at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to re-expand to a predetermined diameter in the vessel.

U.S. Pat. No. 4,886,062 discloses a vascular stent which comprises a length of sinuous or "zig-zag" wire formed into a helix; the helix defines a generally cylindrical wall which, in use, constitutes a prosthetic intraluminal wall. The sinuous configuration of the wire permits radial expansion and compression of the stent; U.S. Pat. No. 4,886,062 discloses that the stent can be delivered percutaneously and expanded in situ using a balloon catheter.

U.S. Pat. No. 4,733,665 discloses an expandable intraluminal graft which is constituted by a tubular member formed from a plurality of intersecting elongate members which permit radial expansion and compression of the stent.

EP-A-0556850 discloses an intraluminal stent which is constituted by a sinuous wire formed into a helix; juxtaposed apices of the wire are secured to one another so that each hoop of the helix is supported by its neighboring hoops to increase the overall strength of the stent and to minimize the risk of plaque herniation; in some embodiments, the stent of EP-A-0556850 further comprises a tubular graft member to form an endoluminal prosthesis.

The devices cited above are generally satisfactory for the treatment of aneurysms, stenoses and other angeological diseases at sites in continuous unbifurcated portions of arteries or veins.

Within the vasculature, however, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents, however, are not wholly satisfactory for use where the site of desired application of the stent is juxtaposed or extends across a bifurcation in an artery or vein, for example, such as the bifurcation in the mammalian aortic artery into the common iliac arteries.

In the case of an abdominal aortic aneurysm ("AAA") in the infrarenal portion of the aorta which extends into one of the common iliac arteries, the use of one of the prior art prosthesis referred to above across the bifurcation into the one iliac artery will result in obstruction of the proximal end of the other common iliac artery; by-pass surgery is therefore required to connect the one iliac artery in juxtaposition with the distal end of the prosthesis to the other blocked iliac artery. It will be appreciated by a person skilled in the art that it is desirable to avoid surgery wherever possible; the requirement for by-pass surgery associated with the use of the prior art prosthesis in juxtaposition with a bifurcation in an artery therefore constitutes a significant disadvantage.

Another example of a vessel bifurcation is the left and right common carotid arteries. These arteries are the principal arteries of the head and neck. Both of the common carotid arteries are quite similar and divide at a carotid bifurcation or bulb into an external carotid artery and an internal carotid artery. In the region of the carotid bulb and the ostium of the internal carotid artery, stenoses present a particular problem for carotid stenting due to the large tapering of the vessel interior from the common carotid artery (both the left and the right) to the internal carotid artery. The region of the carotid bifurcation or bulb happens to be where stenoses most often occur, particularly in the region of the ostium to the internal carotid artery in both of the carotid arteries.

Embodiments of the present invention relate to endoluminal prosthesis (stents) that may be utilized in the region of a bifurcation of vessels. The present invention also embraces stent connecting means for connecting a stent (e.g., a stent which forms part of an endoluminal prosthesis or bifurcated stent) to another stent or portion thereof. Some embodiments of the invention are directed to designs of bifurcated stents and their method of manufacture, as well as apparatuses and methods for introducing prostheses to the vasculature and methods of treating angeological diseases.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention includes many different embodiments. Various embodiments of the invention are directed to designs of bifurcated stents and/or the methods and apparatuses utilized to deliver a bifurcated stent to a bifurcation site.

In some embodiments, the invention is directed to a bifurcated stent assembly having a unique engagement mechanism for joining two stent bodies together when in the expanded state. In some embodiments, the engagement mechanism may be a plurality of stent members that form a scaffold which extends into the ostium of the secondary vessel when the primary stent body is expanded. The scaffold provides a conduit for the introduction of the secondary stent body into the secondary vessel through the primary stent. The scaffold also provides at least a partial lining of the transition area between the stent bodies. In some embodiments where the scaffold is at least partially constructed from metal, one or more of the members may be at least partially selectively annealed to provide the scaffold with improved flexibility and actuation.

In at least one embodiment of the invention, a scaffold equipped primary stent body may be expanded and delivered via a unique inflation member or balloon having a unique geometry. When inflated to expand the primary stent, the geometry of the balloon is characterized by a bulge region that allows the scaffold portion to be expanded prior to or subsequent to the expansion of the rest of primary stent body. In at least one embodiment, the bulge region is defined as a thicker or thinner portion balloon wall.

In at least one embodiment, the scaffold is defined by a plurality of self-expanding members, wherein the members are constructed and arranged to outwardly expand from the primary stent body to define the side opening and a flow path therethrough.

In at least one embodiment, the invention is directed to a bifurcated stent delivery system that includes one or more catheter assemblies comprising two guide wires, a primary and secondary guide wire for delivering two stent bodies to a bifurcation of vessels. The catheter (or catheters) is configured to allow a first stent body to be advanced along the first guide wire to the primary vessel of the bifurcation site where it is positioned to extend across the secondary vessel or daughter branch of the bifurcation with a side opening exposed thereto. The secondary guide wire is constructed and arranged to be advanced through the partially expanded first stent body and through the side opening to enter the secondary vessel of the bifurcation. The second stent body may then be advanced along the secondary guide wire through the side opening of the expanded first stent body for positioning into the secondary vessel. In at least one embodiment, the stent bodies are configured such that during positioning and/or expansion of the secondary stent body, the secondary body becomes engaged to at least a portion of the first stent body defining the side opening.

In some embodiments, the first stent section and/or the second stent section employs one or more engagement members for engaging the stent bodies to each other when fully expanded. Preferably, the engagement members define a scaffold as previously described.

In some embodiments, the stent bodies may each be balloon expandable, self-expandable, or hybrid expandable.

In some embodiments, the catheter may comprise one or more expandable members or balloons for expanding and/or seating the stent bodies.

In another embodiment, the invention is directed to a bifurcated stent delivery system comprising a first catheter and a second catheter. The first catheter is configured to deliver a first stent body around the contra lateral wall of a bifurcation site such that the first stent body extends from a primary vessel into the secondary vessel of the bifurcation. A proximal portion of the first stent body is constructed and arranged to be positioned proximal to the carina of the bifurcation, the distal portion of the bifurcated stent is constructed and arranged to extend from the proximal portion into the secondary vessel around the contra lateral wall of the bifurcation. When properly positioned about the contra lateral wall, the side opening of the first stent body is positioned adjacent to the carina of the bifurcation site to provide an open flow path through the primary vessel and proximal portion of the first stent body. Through this primary flow path a second stent body may be positioned and expanded.

In at least one embodiment, when deployed the second stent body extends proximally and distally into the primary vessel extending from the primary flow path defined by the first stent body. Alternatively, in the deployed state the second stent may be positioned to extend only distally or proximally from the first stent body.

In at least one embodiment, the second stent engages the portion of the first stent that defines the side opening of the bifurcated stent.

In a least one embodiment the side opening of the first stent body is at least partially defined by a scaffold which is constructed and arranged to engage an end of the second stent body in the expanded state.

In some embodiments, the invention is directed to a stent delivery system which delivers two separate stent bodies to a bifurcation site to form a bifurcated stent assembly. The system comprises a single catheter which has at least two stent retaining regions in linear arrangement. The catheter is constructed and arranged to be advance to a bifurcation site, where a distally mounted stent equipped with at least one side opening is deployed from the first stent retaining region. The catheter may then be withdrawn from within the deployed stent and re-advanced through the side opening of the stent into the secondary vessel of the bifurcation site. The second stent may then be deployed from the proximally positioned stent retaining region for deployment into the secondary vessel.

In at least one embodiment, the primary stent comprises a scaffold which extends into the secondary vessel for engagement with the deployed second stent.

In some embodiments, the first stent and the second stent are immediately adjacent to one another in the deployed state.

In some embodiments, the deployed stents remain unengaged in the deployed state. Once both stents are deployed from the catheter, the catheter may be withdrawn from the deployed stents and bifurcation site.

In the various embodiments of the invention, portions of a given catheter and/or stent may include radiopaque materials to aid in visual inspection and/or placement of the devices such as during fluoroscopy.

Additional details and/or embodiments of the invention are discussed below.

BRIEF DESCRIPTION OF THE SEVERAL VIEWS OF THE DRAWINGS

A detailed description of the invention is hereafter described with specific reference being made to the drawings.

DETAILED DESCRIPTION OF THE INVENTION

As indicated above, the present invention includes many different embodiments. In some embodiments, the invention is directed to various designs of bifurcated stents, their delivery systems and methods of use.

Figure 1:
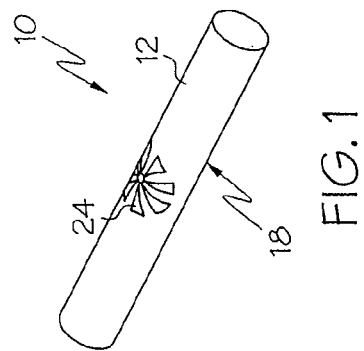
FIG. 1 is a perspective view of an embodiment of the invention directed to a stent shown in the unexpanded state.

In FIG. 1 an embodiment of the invention is shown which comprises a stent, shown generally at 10. Stent 10 is configured to be mounted on a stent delivery catheter for insertion into a body lumen or vessel and advancement to a bifurcation site.

Stent 10 is generally a tubular body having an expandable framework that is self-expandable or balloon expandable. An example of a stent is described in U.S. Pat. No. 6,348,065. When deployed from a catheter, stent 10 may be expanded from an unexpanded state shown in FIG. 1 to an expanded state shown in FIG. 2.

In the unexpanded state shown in FIG. 1, the stent 10 maintains a generally tubular shape defined by a stent body 12. When in the expanded state shown in FIG. 2, however, a scaffold or stent segment 14 extends radially outward from the stent body 12 and defines an opening 16 through the wall 18 of the stent body 12. The opening 16 allows a secondary flow path 22, defined by the scaffold 14, to be in fluid communication with the primary flow path 20 that is defined by the stent body 12.

Figure 2:
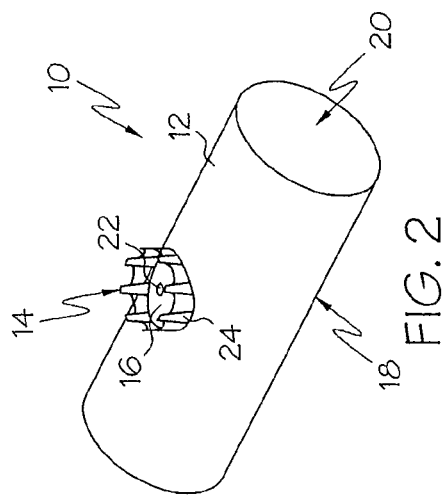
FIG. 2 is a perspective view of the embodiment shown in FIG. 1 wherein the stent is shown in the expanded state.

As is shown in FIGS. 1 and 2, the unique side opening 16 is defined by a scaffold 14. Scaffold 14 is defined by a plurality of stent members 24 which, in the unexpanded state shown in FIG. 1, are contained substantially within the plane of the stent wall 18. When the stent 10 is expanded to the expanded state shown in FIG. 2, members 24 radially expand outward from the stent body 12 to form the scaffold 14.

In at least one embodiment, the stent 10 is constructed at least partially from metal. Preferably, the members 24 are selectively annealed metal to provide for improved flexibility and actuation.

In at least one embodiment, the members 24 are constructed from one or more shape memory materials that allow the members 24 to self-expand during expansion of the stent body 12 thereby forming scaffold 14. Suitable shape memory materials may include metals such as nitinol, or shape memory polymers as are known.

Figure 3:
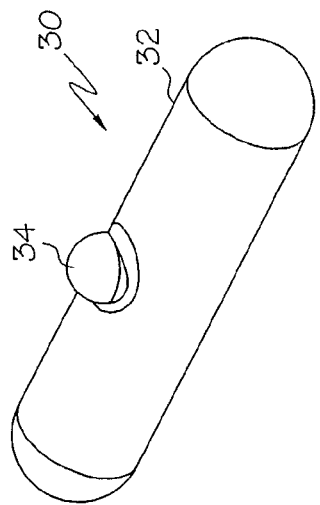
FIG. 3 is a perspective view of an embodiment of the invention directed to a balloon shown in an expanded configuration wherein the balloon includes a bulge region.

In at least one embodiment, the stent 10 may be deployed from a catheter having a unique expansion member or balloon 30, such as is shown in FIG. 3 (shown in an expanded configuration). Balloon 30 may have a body portion 32 that is constructed and arranged to suitably expand the stent body 12. However, in at least one embodiment, balloon 30 also includes a unique geometry which, in the expanded configuration, comprises a bulge region 34 that would effectively push against members 24 to push the members radially outward from the stent body 12 to expand the members 24 to expand outward to form the scaffold 14, or alternatively, where the members 24 are self-expandable the bulge region 34 may be used to trigger the expansion of the members 24 or to lock the members 24 into their final deployed state.

The unique geometry of the balloon 30 allows the scaffold 14 to be deployed prior to or subsequent to the expansion stent body 12. In at least one embodiment, the bulge region 34 is defined as a thicker portion and/or thinner portion of the balloon wall that expands under different pressure and/or inflation characteristics relative to the body portion 32. The characteristics of the bulge region 34 may be varied to allow the scaffold 14 to be deployed prior to, during, or after the expansion of the stent body 12 as desired.

Figure 4:
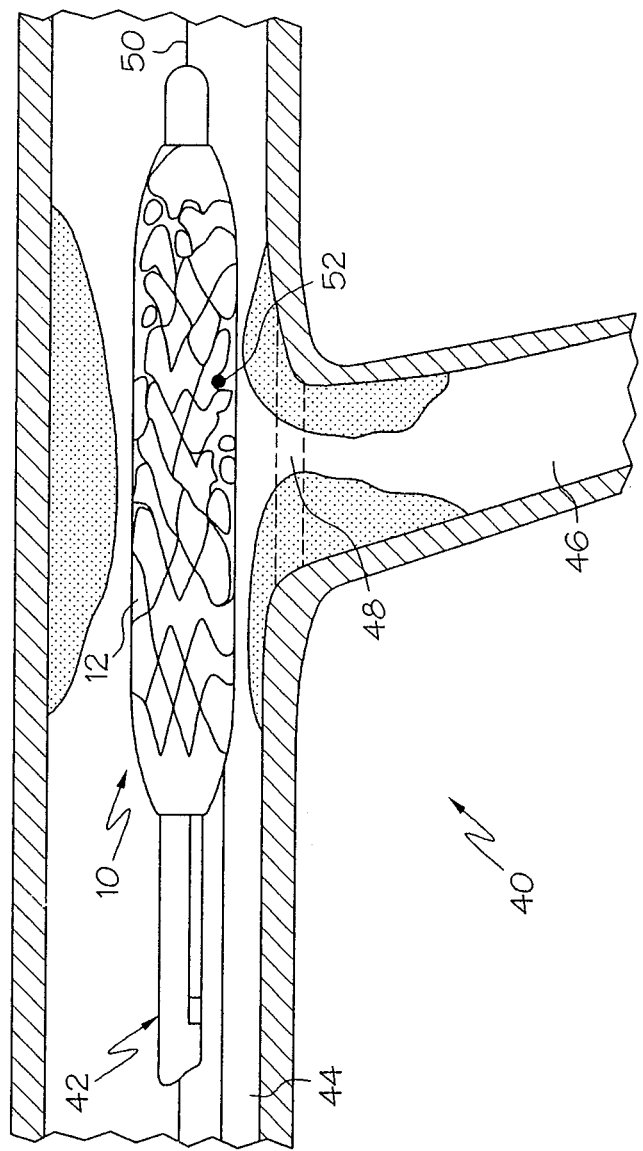
FIG. 4 is a side view of an embodiment of the invention directed to a stent delivery system, the system including a stent delivery catheter shown positioned at a bifurcation site, the catheter having been advanced to the bifurcation site along a primary guide wire, the system including a secondary guide.
Figure 6:
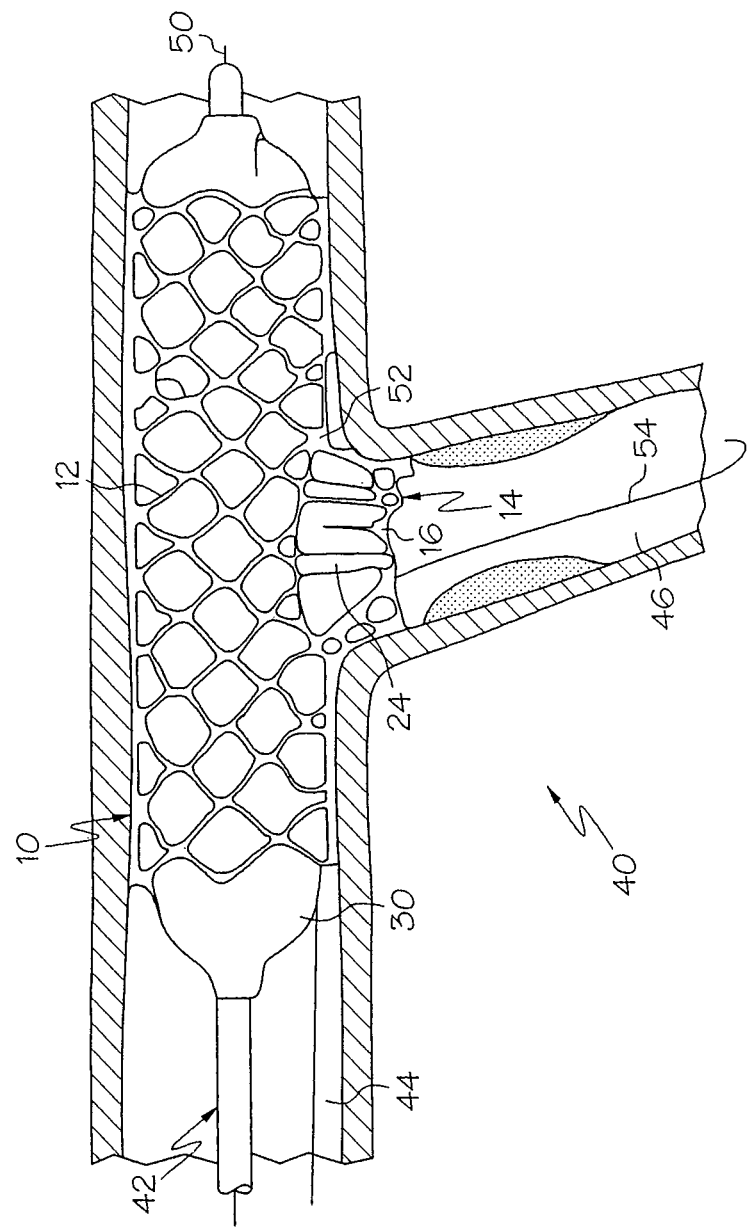
FIG. 6 is a side view of the stent delivery system shown in FIG. 4, wherein a primary stent is shown in a partially expanded state and the secondary guide wire extending through a side opening of the primary stent into the secondary vessel of the bifurcation site.

As may be seen in FIG. 4, the stent 10 may be deployed to a bifurcation site 40 by a catheter 42. The catheter 42 is advanced through a vessel 44 and is positioned at the bifurcation site 40 such that when stent 10 is deployed, as shown in FIG. 6, the scaffold 14 will extend into a secondary vessel or branch 46 and the stent body 12 extends across the ostium 48 of the branch 46.

Typically, catheter 42 is advanced to the bifurcation site 40 along a guide wire 50. In some embodiments, the stent 10 or a portion of the catheter 42 includes a radiopaque marker 52 which is utilized to aid in accurate visual positioning of the catheter and/or stent at the bifurcation site 40, such as by fluoroscopy, etc.

Figure 5:
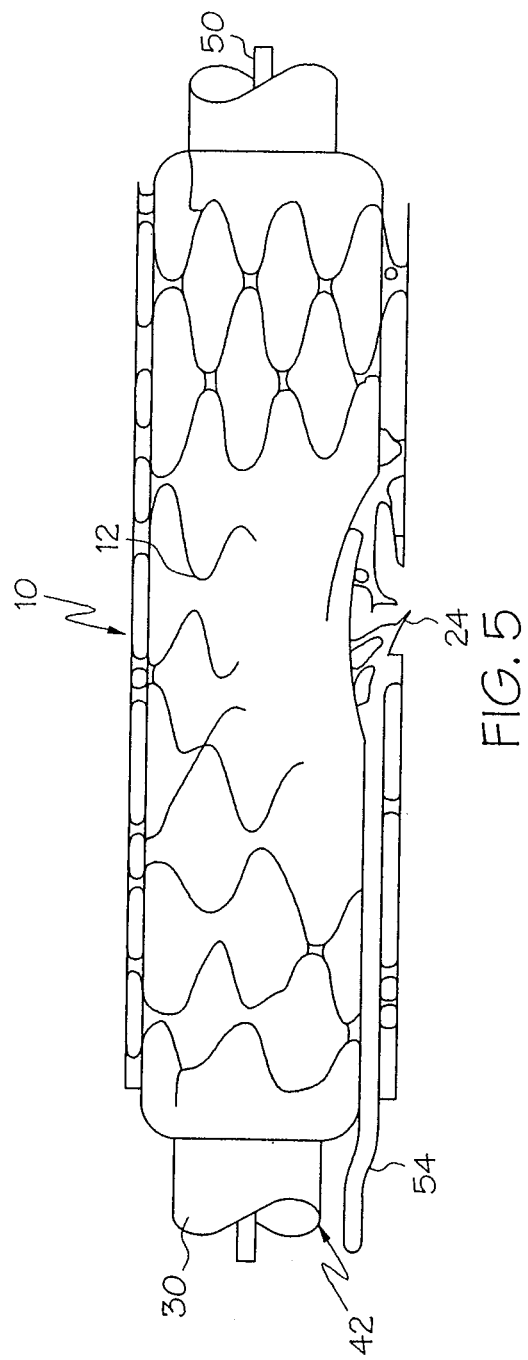
FIG. 5 is a close-up view of the catheter shown in FIG. 4.

In some embodiments, the catheter 42 includes a second guide wire 54 that is advanced at least partially through the stent body 12 as may best be seen in FIG. 5. When the stent 10 is expanded, such as is shown in FIG. 6, the second guide wire 54 is advanced through the side opening 16 into the secondary vessel 46.

Figure 7:
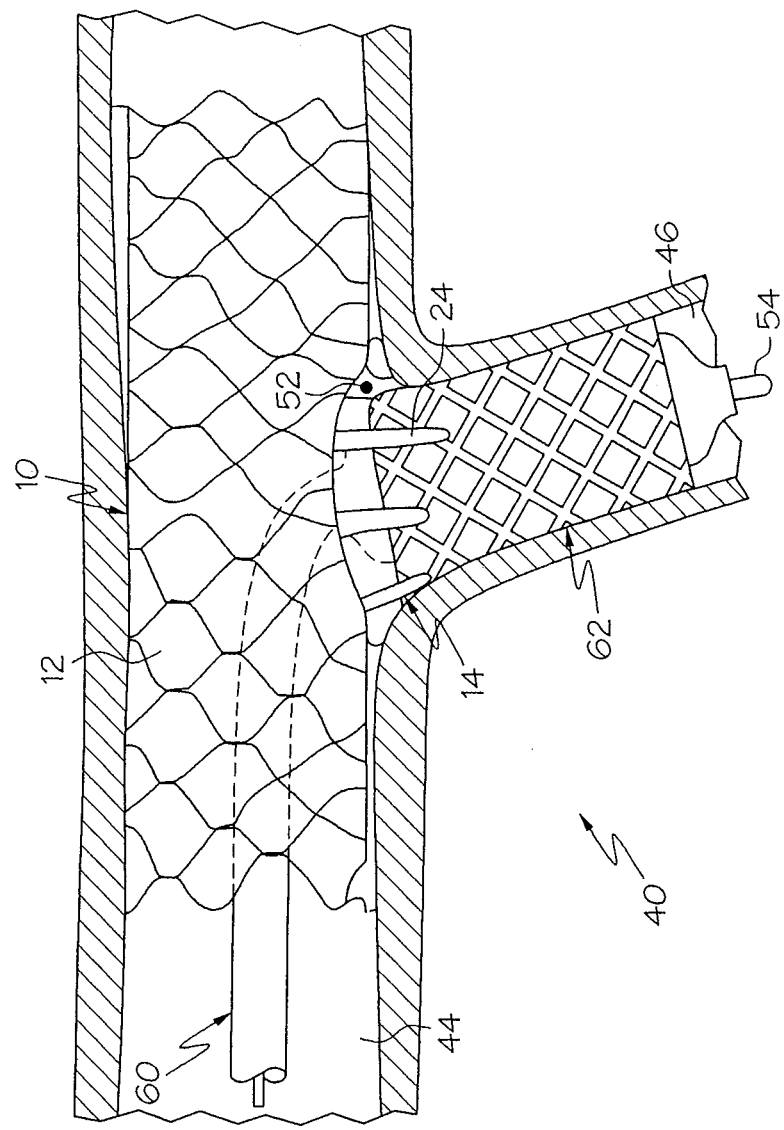
FIG. 7 is a side view of the stent delivery system of FIG. 6 wherein the primary stent is shown in the fully expanded state; a secondary catheter is shown passed through the primary stent into the secondary vessel where a secondary stent is shown partially expanded.

In some embodiments it may be necessary to provide additional stent support to a portion of the secondary vessel 46. In the embodiment shown in FIG. 7, a second catheter 60 is advanced along the second guide wire 54 and is at least partially advanced into the secondary vessel 46. The second catheter 60, has a second stent 62 mounted thereon. Second stent 62 is deployed into the secondary vessel 46 by self-expansion or by balloon expansion, such as is shown.

Figure 8:
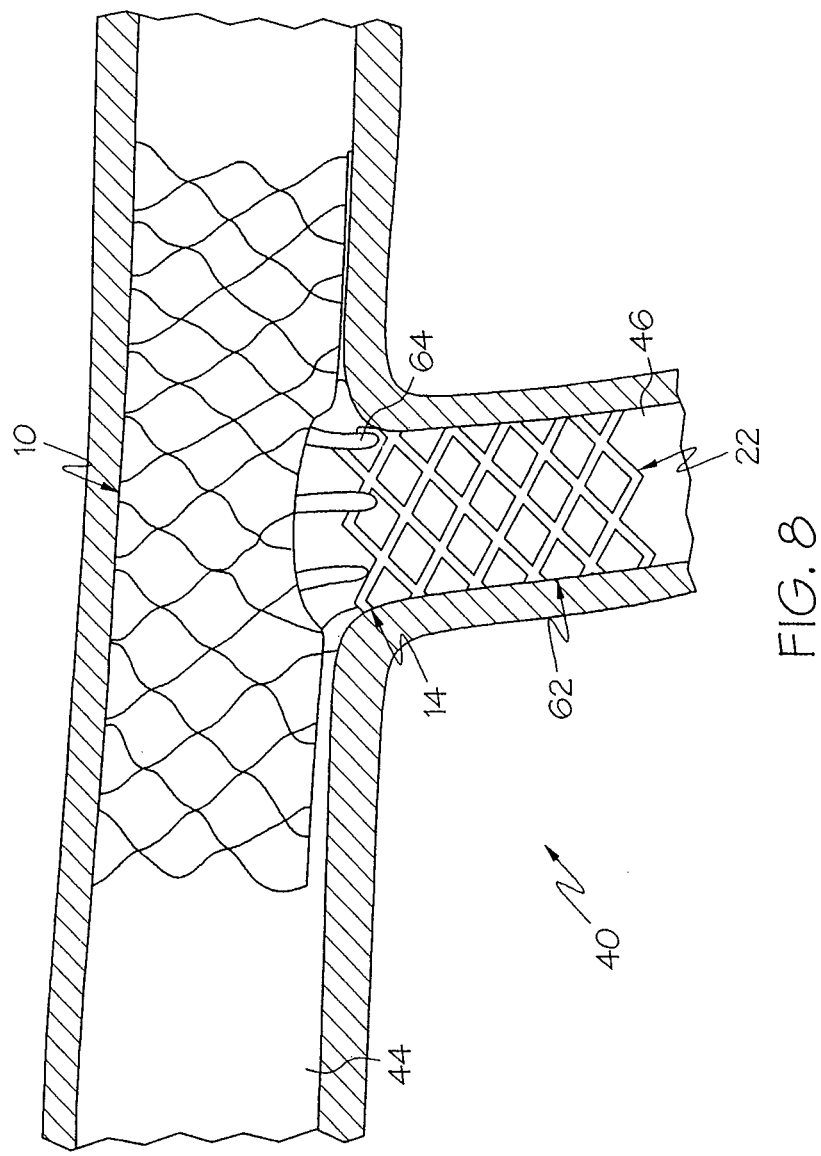
FIG. 8 is a side view of the embodiment shown in FIG. 7 wherein the secondary stent is shown fully expanded, a scaffold structure of the primary stent provides a flow path from the side opening of the primary stent to the secondary stent and is engaged thereto.

In at least one embodiment, such as is shown in FIG. 8, the second stent 62 is positioned within the secondary vessel 46 such that an end 64 of the second stent is engaged by the scaffold 14 when stent 10 and second stent 62 are in the expanded state. The second stent 62 effectively extends and further defines the secondary flow path 22 of the scaffold 14.

Figure 9:
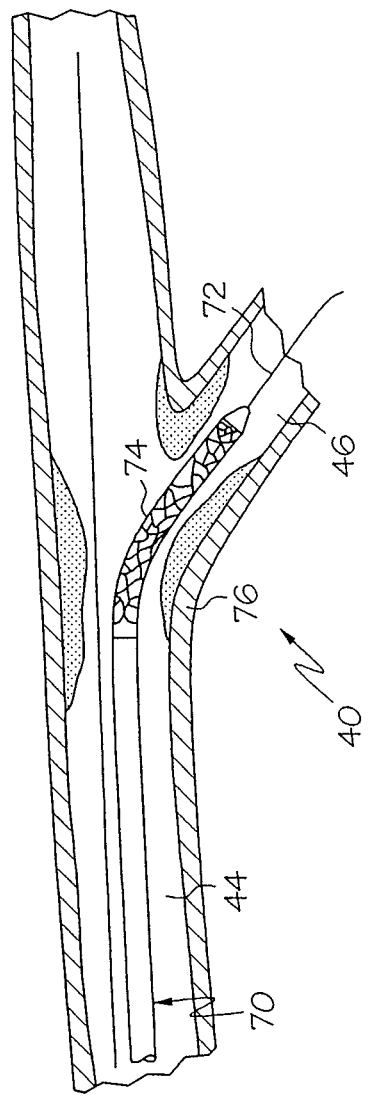
FIG. 9 is a side view of an embodiment of the invention directed to a stent delivery system, the system including a stent delivery catheter shown positioned at a bifurcation site and extending into the secondary vessel of the bifurcation, the catheter having been advanced into the secondary vessel along a guide wire, the system including a second guide wire extending into the primary vessel.

In an alternative embodiment of the invention shown in FIG. 9, a first catheter 70 is advanced along a first guide wire 72 which extends through the primary vessel 44 and into the secondary vessel 46. Catheter 70 includes a first stent body 74 which is retained on the catheter 70 in an unexpanded state. First catheter 70 is advanced to the bifurcation site 40 such that the first stent body 74 is positioned for delivery against the contra lateral wall 76 of a bifurcation site such that the first stent body 74 extends from a primary vessel 44 into the secondary vessel 46 of the bifurcation 40.

Figure 10:
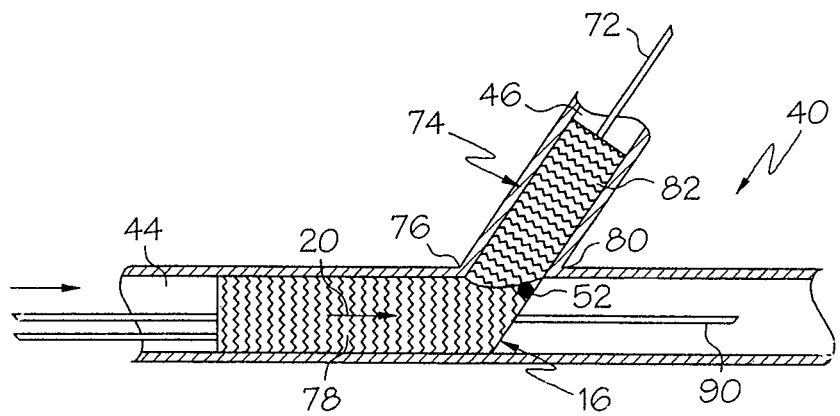
FIG. 10 is a side view of an embodiment of a primary stent deployed by the catheter shown in FIG. 9.

When the first stent body 74 is deployed, such as is shown in FIG. 10, a proximal portion 78 of the first stent body 74 is positioned proximal to the carina 80 of the bifurcation 40. A distal portion 82 of the first stent body 74 is positioned to extend from the proximal portion 78 into the secondary vessel 44 against the contra lateral wall 76 of the bifurcation 40. Proper positioning of the first stent body 74 and/or catheter 70 may be assisted through the use of one or more radiopaque markers 52 such as described above.

In the expanded state, first stent body 74 includes a side opening 16 such as previously described. When properly positioned about the contra lateral wall 76, the side opening 16 is positioned adjacent to the carina 80 to provide a primary flow path 20 through the proximal portion 78 of the first stent body in fluid communication with the primary vessel 44. Through the primary flow path 20 a second guide wire 90 may be advanced.

Figure 11:
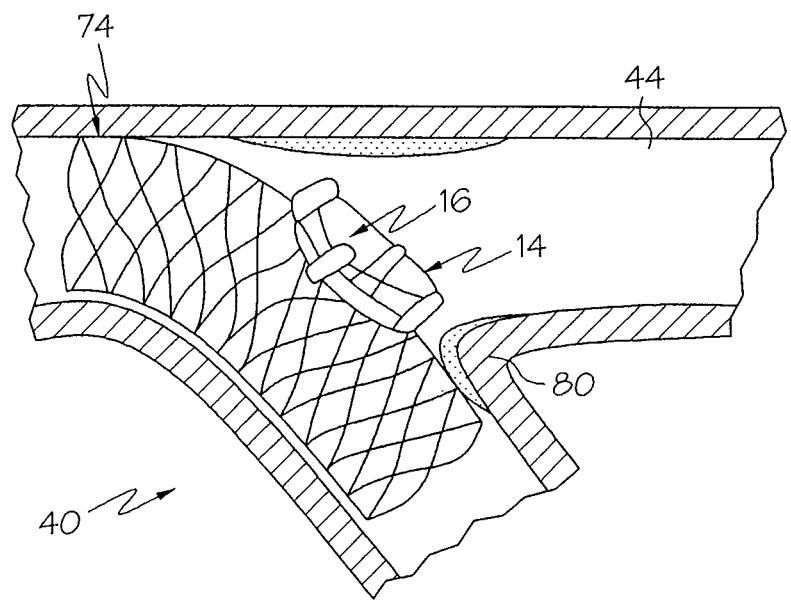
FIG. 11 is a side view of an embodiment of a primary stent deployed by the catheter shown in FIG. 9.

In at least one embodiment of the invention such as is shown in FIG. 11, the side opening 16 is defined by a scaffold 14 such as previously described. In the present embodiment, in the expanded state the scaffold 14 will extend into the primary vessel 44. When the first stent body 74 is deployed the scaffold may be positioned proximally adjacent to the carina 80. In at least one embodiment, the scaffold 12 may be constructed to extend across the carina 80.

Figure 12:
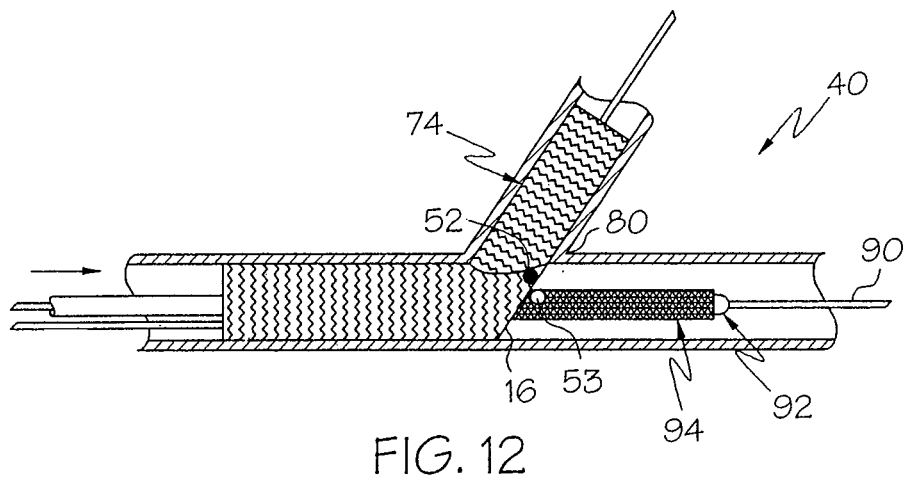
FIG. 12 is a side view of the embodiments shown in FIG. 10 or 11 wherein the system further includes a second catheter which is advanced through the proximal portion of the deployed stent through a side opening in the deployed stent.

After the first stent body 74 is properly positioned and deployed at the bifurcation site 40, in some embodiments a second stent delivery catheter 92 is advanced along the second guide wire 90 to position a second stent body 94 through the side opening 16 such as is shown in FIG. 12. In some embodiments, the second catheter 92 and/or stent body 94 includes a second radiopaque marker 53 to aid in positioning the second catheter 92 and/or stent body 94 relative to the expanded first stent body 74.

Figure 13:
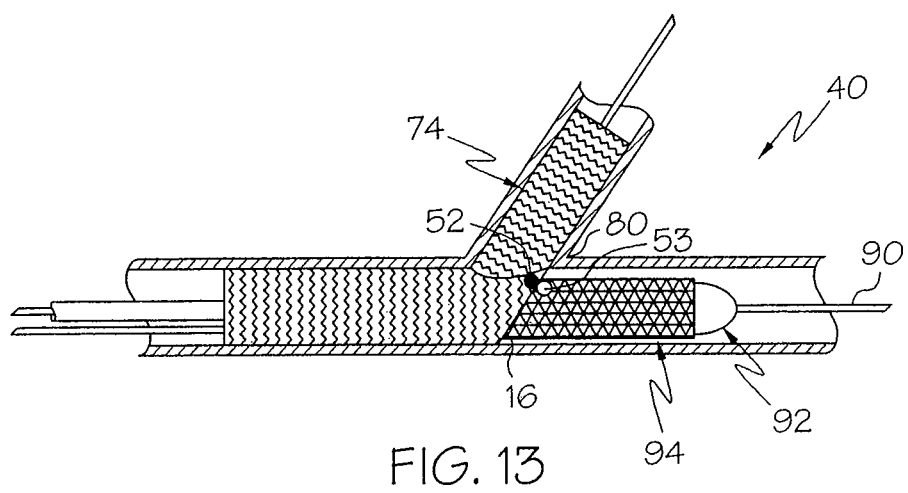
FIG. 13 is a side view of a second catheter shown in FIG. 12, shown deploying a second stent through the side hole of the previously deployed stent.

In at least one embodiment, the second stent body 94 is positioned immediately adjacent to the side opening 16 of the first stent body 74, and is then expanded such as is shown in FIG. 13. As with the first stent body 74, the second stent body 94 may be a self-expanding stent or a balloon expandable stent as desired.

Figure 14:
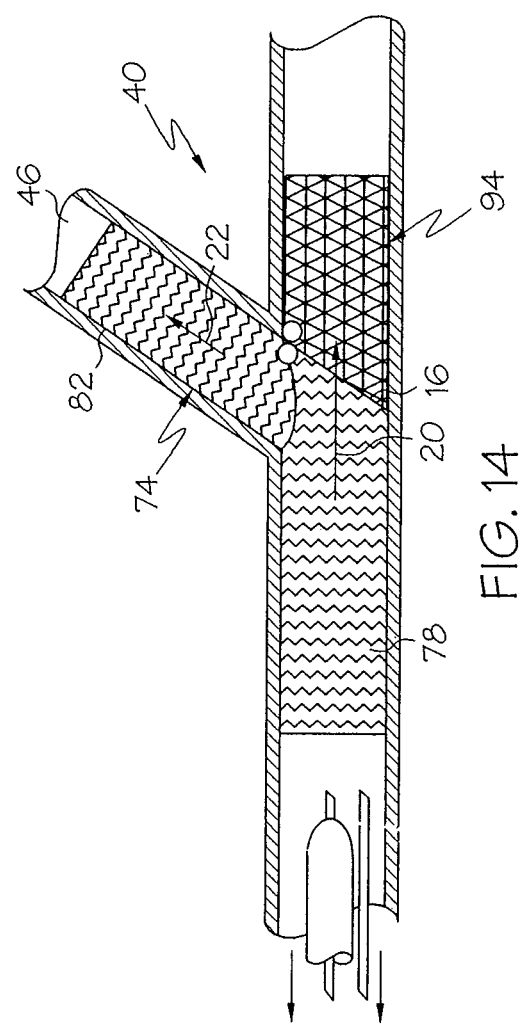
FIG. 14 is a side view of an embodiment of the invention wherein a first stent section is deployed at a bifurcation site to extend from a primary vessel into a secondary vessel across the contra lateral wall of the ostium, and a second stent is deployed through the side opening of the first stent and is engaged thereto to extend from the carina into a distal portion of the primary vessel.

When the first stent body 74 and second stent body 94 are fully expanded, such as is shown in FIG. 14, the proximal portion 78 of the first stent body 74 and the second stent body 94 effectively define a continuous primary flow path 20 via the side opening 16. The distal portion 82 of the first stent body 74 defines the secondary flow path 22 within the secondary vessel 46 that is in fluid communication with the primary flow path 20.

Figure 15:
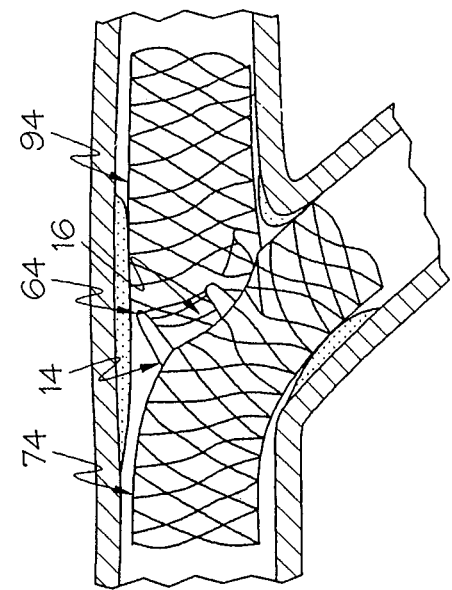
FIG. 15 is a side view of an embodiment of the invention wherein a first stent section is deployed at a bifurcation site to extend from a primary vessel into a secondary vessel across the contra lateral wall of the ostium, and a second stent is deployed through the side opening of the first stent to extend from the carina into a distal portion of the primary vessel, the first stent being engaged to the second stent via a scaffold structure extending from the first stent.
Figure 16:
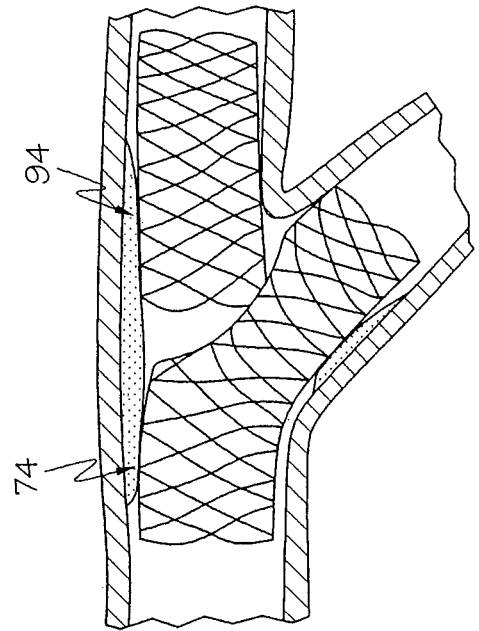
FIG. 16 is a side view of an embodiment of the invention wherein a first stent section is deployed at a bifurcation site to extend from a primary vessel into a secondary vessel across the contra lateral wall of the ostium, and a second stent is deployed through the side opening of the first stent and is adjacent thereto to extend from the carina into a distal portion of the primary vessel.

As indicated above, in some embodiments, the second stent body 94 is positioned to be immediately adjacent to the first stent body 74 such as is shown in FIG. 14. Bodies 74 and 94 may be frictionally or otherwise engaged to one another. In embodiments where the first stent body 74 includes a scaffold 14, such as is depicted in FIG. 15, the scaffold 14 is engaged to the end 64 of the second stent body 94, such as in the manner previously described. In at least one embodiment of the invention, the end 64 of the second stent body 94 is positioned relative to the side opening 16 of the first stent body 74 in such a manner that the two stent bodies have only a partial engagement, such as is shown in FIG. 16. In at least one embodiment, the stent bodies 74 and 94 remain separate and unengaged in the expanded state.

Figure 17:
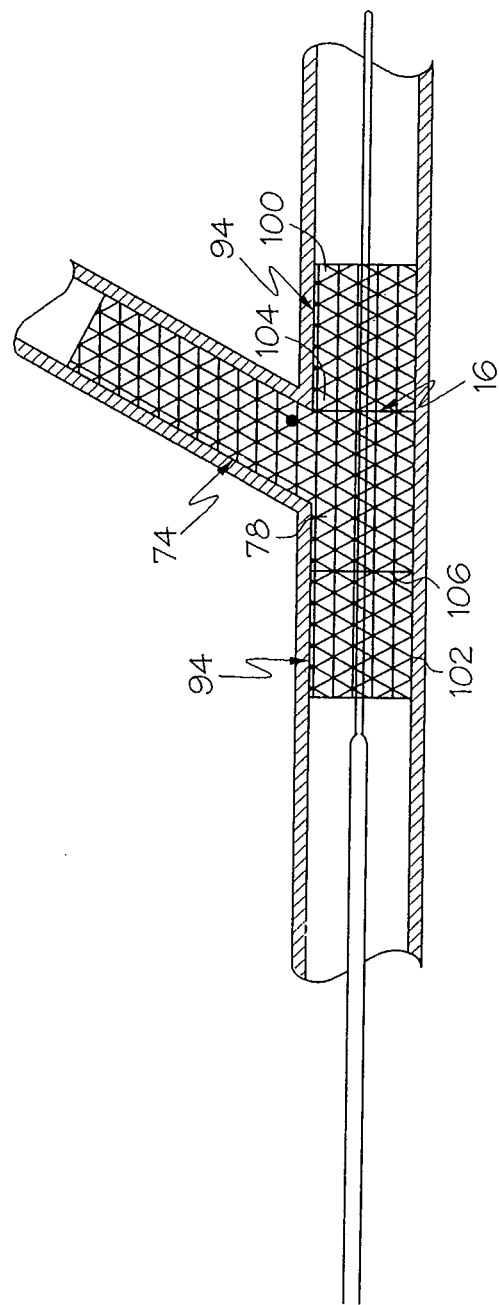
FIG. 17 is a side view of an embodiment of the invention wherein a first stent section is deployed at a bifurcation site to extend from a primary vessel into a secondary vessel across the contra lateral wall of the ostium, and a second stent is deployed through the side opening of the first stent to extend through the flow path defined by the proximal portion of the first stent across the ostium of the secondary vessel.

In at least one embodiment of the invention, it may be desired to provide stent support to the primary vessel both proximally and distally of the proximal portion of the first stent body. In such an embodiment, the second stent body 94 may be a single elongated stent that extends proximally and distally through and beyond the proximal portion 78 of the first stent body 74, such as is shown in FIG. 17. In an alternative embodiment, the second stent body 94 comprises a first portion 100 and a second portion 102. Prior to expansion and deployment, first portion 100 may be advanced through the proximal portion 78 of the first stent body 74 for positioning immediately distal of the side opening 16. The second portion 102 may be positioned and deployed immediately proximal to the proximal portion 78 of the first stent body 74. Portions 100 and 102 may be engaged to one another or may define separate and distinct stent bodies. The portions 100 and 102 may be respectively engaged to ends 104 and 106 of the proximal portion 78 of the first stent body 74 or they may be separate therefrom. Portions 100 and 102, like all of the stent bodies described herein, may be balloon expandable, self-expandable, hybrid expandable or have a combination of expansion characteristics.

Figure 18:
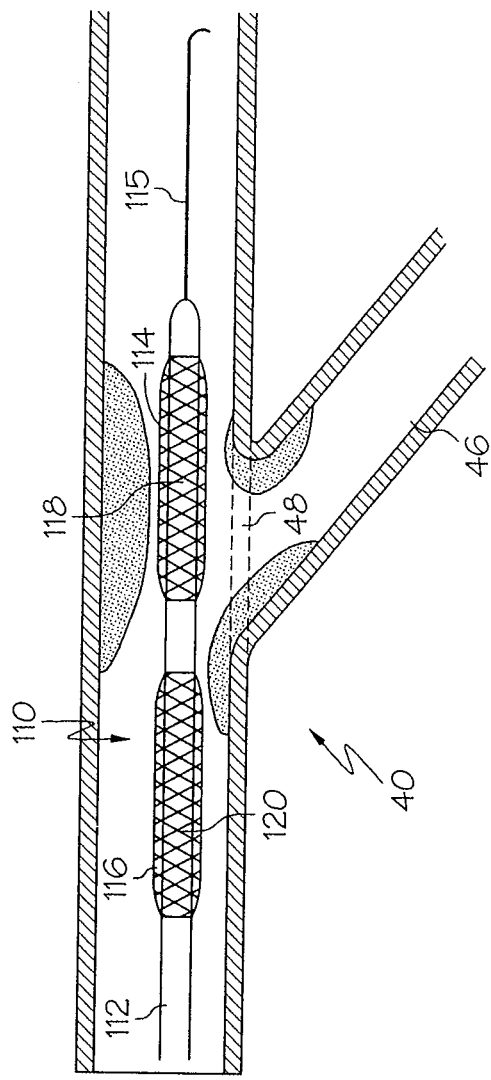
FIG. 18 is a side view of an embodiment of the invention directed to a catheter for delivering a bifurcated stent assembly to a bifurcation site.

In some embodiments, the invention is directed to a stent delivery system, shown generally at 110 in FIG. 18, which includes a single stent delivery catheter 112 that may be utilized to deliver two separate stent bodies 114 and 116 to a bifurcation site 40 to form a bifurcated stent assembly. In the embodiment shown, catheter 112 defines at least two stent retaining regions 118 and 120 for retaining the stent bodies 114 and 116 in the unexpanded state on the catheter 112. As is shown, the stent bodies 114 and 116 are positioned on the catheter 112 in linear series with a first stent body 114 positioned distally in front of the second stent body 116.

In at least one embodiment, the distally mounted stent 114 includes a side opening 16 such as previously described.

Figure 19:
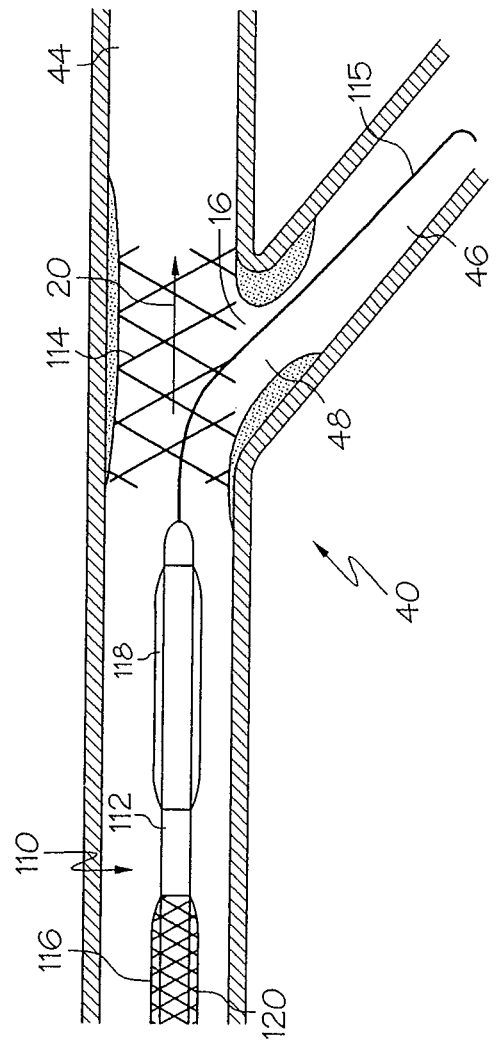
FIG. 19 is a side view of the catheter shown in FIG. 18 wherein a first stent body having a side opening is deployed across the ostium of a secondary vessel.

In use, the catheter 112 is advanced along a guide wire 115 through the vasculature to a bifurcation site 40. The first or distally mounted stent body 114 is deployed in at a desired location, preferably adjacent to the ostium 48 of the secondary vessel 46, and more preferably at least partially across the ostium 48 such as is shown in FIG. 19.

Figure 20:
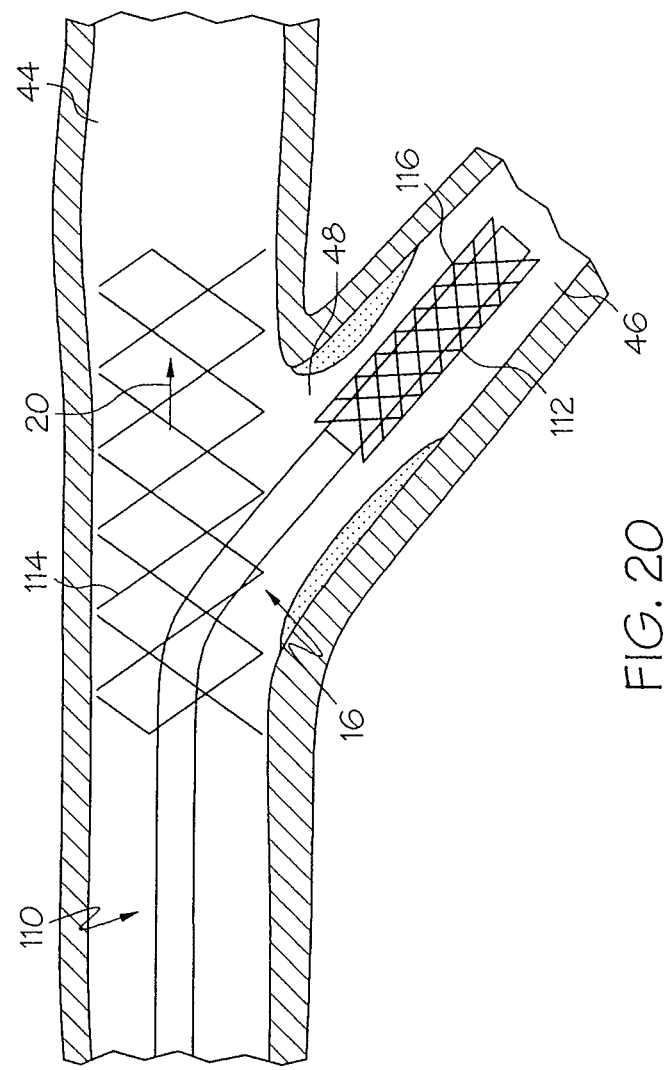
FIG. 20 is a side view of the catheter shown in FIG. 19 wherein the catheter is advanced back through the first stent body through the side opening and into the secondary vessel.

After the first stent body 114 is deployed the guide wire and stent is at least partially withdrawn from the expanded first stent body 114, and then advanced through the primary flow path 20 defined by the first stent body 114, through the side opening 16, and into the secondary vessel 46. Catheter 112 is then advanced along the repositioned guide wire 115 into the secondary vessel 46, such as is shown in FIG. 20. The catheter 112 is positioned to deploy the second stent body 116 at a desired location within the secondary vessel 46. After both stent bodies have been deployed, the catheter 112 may be withdrawn from the body. In a preferred embodiment, the first stent body 114 includes a scaffold such as previously described for engaging an end of the second stent body when deployed.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A medical device comprising:
   a catheter shaft including a proximal region and a distal region; and
   a balloon disposed about a distal region of the catheter shaft, wherein the balloon includes a body region and only a single pre-formed bulge region that protrudes radially outward from the body region when the balloon is expanded without a stent thereon, wherein the single pre-formed bulge region is positioned at a location between a proximal end and a distal end of the body region, wherein the single pre-formed bulge region is formed at a predetermined location around a circumference of the body region and extends around less than the entire circumference of the body region.

2. The medical device of claim 1, wherein the pre-formed bulge region is configured to have different pressure and/or inflation characteristics than the body region of the balloon.

3. The medical device of claim 2, wherein the pre-formed bulge region is configured to expand after the body region.

4. The medical device of claim 2, wherein the pre-formed bulge region is configured to expand prior to the body region.

5. The medical device of claim 1, wherein the pre-formed bulge region has a first thickness that is greater than a second thickness of the body region of the balloon.

6. The medical device of claim 1, wherein the pre-formed bulge region has a first thickness that is less than a second thickness of the body region of the balloon.

7. The medical device of claim 1, further comprising a stent disposed around at least a portion of the balloon, the stent including a stent body having a substantially tubular stent wall defining a circumferential plane and a plurality of movable members engaged to the stent wall, the stent body being expandable from an unexpanded condition to an expanded condition by expansion of the balloon, in the unexpanded condition the plurality of movable members being retained substantially within the circumferential plane of the stent wall and aligned with the pre-formed bulge region of the balloon, and in the expanded condition, a portion of the plurality of movable members being extended radially outward from the stent wall by the expansion of the pre-formed bulge region of the balloon to define a side opening in the stent wall.

8. The medical device of claim 7, wherein each of the moveable members are moveable independent of the other moveable members.

9. The medical device of claim 7, wherein the plurality of movable members are self-expandable, balloon expandable, or hybrid expandable.

10. The medical device of claim 7, wherein at least a portion of the stent is constructed from a shape-memory material.

11. The medical device of claim 7, wherein the movable members include a shape memory material, and expansion of the pre-formed bulge region of the balloon within the stent body activates the shape memory material to move the movable members into the radially outward extended position.

12. A medical device comprising:
a catheter including a balloon, the balloon including a body portion and only a single pre-formed bulge portion configured to protrude radially outward from the body portion when the balloon is expanded without a stent thereon, the pre-formed bulge portion being positioned at a location between a proximal end and a distal end of the body portion, wherein the pre-formed bulge portion extends around less than an entire circumference of the body portion, wherein the body portion and the pre-formed bulge portion have different inflation characteristics.

13. The medical device of claim 12, wherein the body portion and the pre-formed bulge portion are configured to expand simultaneously.

14. The medical device of claim 12, wherein the pre-formed bulge portion is configured to expand after the body portion.

15. The medical device of claim 12, wherein the pre-formed bulge portion is configured to expand before the body portion.

16. The medical device of claim 12, further comprising a stent disposed around at least a portion of the balloon, the stent including a stent body having a substantially tubular stent wall defining a circumferential plane and a plurality of movable members engaged to the stent wall, the stent body being expandable from an unexpanded condition to an expanded condition by expansion of the balloon, in the unexpanded condition the plurality of movable members being retained substantially within the circumferential plane of the stent wall and aligned with the pre-formed bulge portion of the balloon, and in the expanded condition, a portion of the plurality of movable members being extended radially outward from the stent wall by the expansion of the pre-formed bulge portion of the balloon to define a side opening in the stent wall.

17. A medical device comprising:
a catheter including a balloon, the balloon including a body portion and only a single pre-formed bulge portion configured to protrude radially outward from the body portion when the balloon is expanded without a stent thereon, the pre-formed bulge portion being positioned at a location between a proximal end and a distal end of the body region, wherein the pre-formed bulge portion extends around less than an entire circumference of the body portion, wherein the body portion is configured to be expanded before or after the pre-formed bulge portion when the balloon is inflated.

18. The medical device of claim 17, further comprising a stent disposed around at least a portion of the balloon, the stent including a stent body and a plurality of movable members, wherein the plurality of movable members are positioned over the pre-formed bulge portion such that in an expanded condition, the plurality of movable members are configured to extend radially outward from the stent wall to form a scaffold defining a side opening in the stent wall.

19. The medical device of claim 18, wherein each of the plurality of moveable members are moveable independent of the other moveable members.

20. The medical device of claim 18, wherein at least a portion of the stent is constructed from a shape-memory material.

* * * * *